(12) United States Patent
Ries et al.

(10) Patent No.: US 8,216,134 B2
(45) Date of Patent: Jul. 10, 2012

(54) IMPLANTABLE OPTICAL SENSOR AND METHOD FOR MANUFACTURE

(75) Inventors: Andrew J. Ries, Lino Lakes, MN (US); Jeffrey O. York, Mesa, AZ (US); Stephen R. Belcher, Fountain Hills, AZ (US); Jeffrey M. Jelen, New Hope, MN (US)

(73) Assignee: Medtronic, Inc., Minneapolis, MN (US)

( * ) Notice: Subject to any disclaimer, the term of this patent is extended or adjusted under 35 U.S.C. 154(b) by 1099 days.

(21) Appl. No.: 12/116,705

(22) Filed: May 7, 2008

(65) Prior Publication Data
US 2009/0156905 A1 Jun. 18, 2009

Related U.S. Application Data

(63) Continuation-in-part of application No. 11/955,039, filed on Dec. 12, 2007, now abandoned.

(51) Int. Cl.
*A61B 5/00* (2006.01)
(52) U.S. Cl. .............. 600/300; 600/310; 607/5; 257/433
(58) Field of Classification Search .......... 600/300–301, 600/339, 333, 322–325, 341, 328, 344, 372, 600/472, 476; 607/22, 122
See application file for complete search history.

(56) References Cited

U.S. PATENT DOCUMENTS

| | | | |
|---|---|---|---|
| 3,985,449 A | 10/1976 | Patrin et al. | |
| 4,100,562 A | 7/1978 | Sugawara et al. | |
| 4,202,339 A | 5/1980 | Wirtzfeld et al. | |
| 4,467,807 A | 8/1984 | Bornzin | |
| 4,730,389 A | 3/1988 | Baudino et al. | |
| 4,972,254 A * | 11/1990 | Endo et al. | 348/275 |
| 5,010,381 A | 4/1991 | Shiba et al. | |
| 5,144,381 A | 9/1992 | Furnyama et al. | |
| 5,556,421 A | 9/1996 | Prutchi et al. | |
| 5,902,326 A | 5/1999 | Lessar et al. | |
| 6,125,290 A | 9/2000 | Miesel et al. | |
| 6,198,952 B1 | 3/2001 | Miesel et al. | |
| 6,409,675 B1 | 6/2002 | Turcott | |
| 6,491,639 B1 | 12/2002 | Turcott | |

(Continued)

FOREIGN PATENT DOCUMENTS
WO 2009076063 A1 6/2009

OTHER PUBLICATIONS
PCT International Search Report; PCT/US2009/042764.

*Primary Examiner* — Sam Yao
*Assistant Examiner* — Marie Archer
(74) *Attorney, Agent, or Firm* — Michael C. Soldner; Stephen W. Bauer; Evans M. Mburu

(57) ABSTRACT

An implantable medical device is manufactured with a hermetically sealed housing and a modular assembly enclosed within the housing. The modular assembly includes a circuit board, an electronic component mounted on a top surface of the circuit board, and a wall formed having an outer surface and an inner surface separated by a top edge and a bottom edge, the wall bottom edge positioned against the circuit board such that the wall encircles the electronic component coupled to the circuit board. The wall top edge is coupled to the housing a ferrule in one embodiment.

26 Claims, 8 Drawing Sheets

U.S. PATENT DOCUMENTS

| | | |
|---|---|---|
| 7,311,449 B2 * | 12/2007 | Barnoski et al. ................ 385/78 |
| 2004/0176669 A1 | 9/2004 | Colvin et al. |
| 2004/0220629 A1 | 11/2004 | Kamath et al. |
| 2005/0179805 A1 * | 8/2005 | Avron et al. ................ 348/340 |
| 2005/0266604 A1 * | 12/2005 | Byquist ........................ 438/73 |
| 2006/0006486 A1 * | 1/2006 | Seo et al. ..................... 257/433 |
| 2009/0076353 A1 * | 3/2009 | Carpenter et al. ............ 600/310 |
| 2009/0156905 A1 | 6/2009 | Ries et al. |

* cited by examiner

IMPLANTABLE OPTICAL SENSOR AND METHOD FOR MANUFACTURE

REFERENCE TO RELATED APPLICATIONS

This application is a continuation-in-part of U.S. patent application Ser. No. 11/955,039, filed Dec. 12, 2007 now abandoned and claims priority therefrom. Cross-reference is hereby made to co-pending U.S. patent application Ser. No. 11/955,025 entitled "IMPLANTABLE OPTICAL SENSOR AND METHOD FOR USE" and U.S. patent application Ser. No. 11/955,056 entitled "IMPLANTABLE OPTICAL SENSOR AND METHOD FOR MANUFACTURE", both applications filed on Dec. 12, 2007.

TECHNICAL FIELD

The invention relates generally to implantable medical devices and, in particular, to implantable optical sensors for sensing physiological conditions.

BACKGROUND

Implantable medical devices (IMDs) for monitoring a physiological condition or delivering a therapy include one or more physiological sensors. Physiological sensors used in conjunction with an IMD provide a signal related to a physiological condition from which a patient state or the need for a therapy can be assessed. Examples of such IMDs include heart monitors, pacemakers, implantable cardioverter defibrillators (ICDs), myostimulators, neurological stimulators, drug delivery devices, insulin pumps, glucose monitors, etc.

Optical sensors are employed in IMDs as physiological sensors configured to detect changes in light modulation by a body fluid or tissue measurement volume due to a change in a physiological condition in the body fluid or tissue. Such optical sensors can be used, for example, for detecting changes in metabolite levels in the blood, such as oxygen saturation levels or glucose level, or changes in tissue perfusion. Monitoring such physiological conditions provides useful diagnostic measures and can be used in managing therapies for treating a medical condition. For example, a decrease in blood oxygen saturation or in tissue perfusion may be associated with insufficient cardiac output or respiratory function. Thus monitoring such signals allows an implantable medical device to respond to a decrease in oxygen saturation or tissue perfusion, for example by delivering electrical stimulation therapies to the heart to restore a normal hemodynamic function. One example of an implantable optical sensor used for monitoring blood oxygen saturation is generally disclosed in commonly assigned U.S. Pat. No. 6,198,952 issued to Miesel, hereby incorporated herein by reference in its entirety. Cardiac pacemakers that respond to changes in blood oxygen saturation as measured by an optical sensor are generally disclosed in U.S. Pat. No. 4,202,339 issued to Wirtzfeld and in U.S. Pat. No. 4,467,807 issued to Bornzin, both of which patents are incorporated herein by reference in their entirety. It is further desirable to provide methods for manufacturing implantable optical sensors in a low cost and time-efficient manner that promotes ease of assembly with an associated IMD.

DETAILED DESCRIPTION

Figure 1:
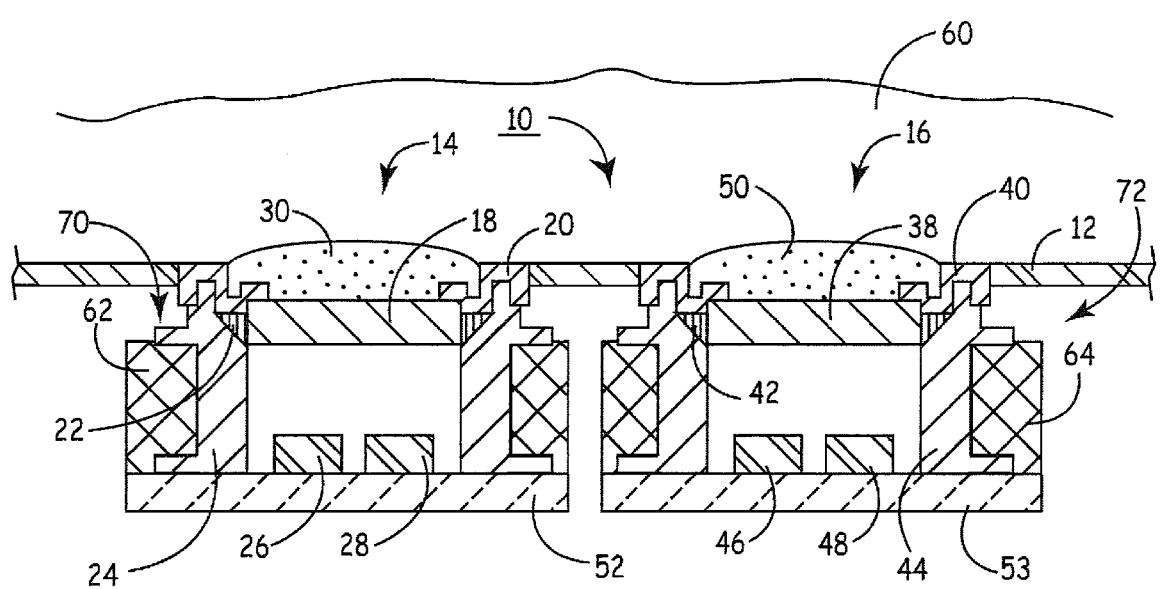
FIG. 1 is side sectional view of an optical sensor according to one embodiment of the invention.

The entire content of U.S. application Ser. No. 11/955,039, filed Dec. 12, 2007, is hereby incorporated by reference.

In the following description, references are made to illustrative embodiments for carrying out the invention. It is understood that other embodiments may be utilized without departing from the scope of the invention. For purposes of clarity, the same reference numbers are used in the drawings to identify similar elements. As used herein, the term "opto-electronic device", also referred to herein as "opto-electronic component", refers to any electrical circuit component capable of emitting light in response to an applied voltage or current or emitting current in response to exposure to light, including for example light emitting diodes (LEDs), vertical cavity surface emitting lasers (VCSELs), photoresistors or light dependent resistors, photodiodes, phototransistors, photovoltaic cells, or charge-coupled devices.

FIG. 1 is side sectional view of an optical sensor 10 according to one embodiment of the invention. Sensor 10 may be incorporated in the housing 12 of an IMD, such as in a subcutaneously implanted pacemaker or ICD housing, or carried by a medical electrical lead. Sensor 10 includes a light emitting portion 14, a light detecting portion 16 configured in a hermetically sealed housing 12 for enclosing optical sensor components and other device circuitry. Each portion 14 and 16 includes a lens 18 and 38, respectively, for passing emitted light from the light emitting portion 14 and scattered light to the light detecting portion 16. Lens 18 and lens 38 are commonly formed from sapphire and are hermetically sealed in openings formed in housing 12 using ferrules 20 and 40, respectively, bonded to lenses 18 and 38 at joints 22 and 42. Joints 22 and 42 may be gold braze joints or formed using a polymer adhesive depending on the ferrule material and other manufacturing processes used in fabricating sensor 10.

Housing 12 may be formed, for example, from titanium, stainless steel, ceramic, glass, or a rigid polymer. In one embodiment, housing 12 and ferrules 20 and 40 are each formed from titanium. Ferrules 20 and 40 are then welded within openings formed in housing 12 to maintain hermeticity of sensor 10 and the implantable device in which sensor 10 is assembled. The optical window assembly generally disclosed in U.S. Pat. No. 5,902,326 (Lessar, et al.), hereby incorporated herein by reference in its entirety, may be implemented in embodiments of the present invention. Transparent polymeric seals 30 and 50 may be formed over lenses 18 and 38 and ferrules 20 and 40, respectively. Seals 30 and 50 may be formed, for example, from silicone rubber or another optically transparent material. Seals 30 and 50 protect gold braze joints 22 and 42 from the corrosive effects of bodily fluids and provide a smooth, convex surface that reduces the susceptibility of sensor 10 to blood clot formation and excessive tissue encapsulation over lenses 18 and 38. Blood clot formation and tissue encapsulation reduces light transmission into and out of sensor 10.

The emitting portion 14 includes a modular sensor assembly 70 coupled to ferrule 20. Modular sensor assembly 70 includes opto-electronic devices 26 and 28, a circuit board 52, a wall 24 surrounding LEDs 26 and 28, and a coating 62 for retaining wall 24 against circuit board 52. Opto-electronic devices 26 and 28 are implemented as light emitting devices, for example as LEDs as referred to hereafter. LEDs 26 and 28 are mounted on a printed circuit board 52 to enable the necessary connections for applying a voltage to each of LEDs 26 and 28 to cause light emission. Wall 24 surrounds the LEDs 26 and 28 to prevent scattering of light and promote transmission of light through lens 18 toward adjacent body fluid or tissue volume 60. Body fluid or tissue volume 60 may correspond to any bodily fluid, such as blood, or body tissue, such as skeletal muscle, neural tissue, myocardium, etc. Wall 24 may be formed from a rigid, light-insulating material, such as a liquid crystal polymer. Alternatively, wall 24 can be formed from other light-insulating materials, for example any polymer material formed as a molded component, and may be non-rigid in some applications. Wall 24 is securely coupled to circuit board 52. As will be further described herein, wall 24 may be coupled to circuit board 52 by applying coating 62 as a hard, die coat dam holding wall 24 to the board 52.

The two LEDs 26 and 28 typically emit light corresponding to two different wavelengths or colors. In one embodiment, in which sensor 10 is used for sensing blood oxygen saturation, one of LEDs 26 and 28 emits red light (660 nm) and the other emits infrared light (890 nm). In another embodiment, in which sensor assembly 10 is used for sensing tissue perfusion, a third LED may be included emitting near-infrared light (800 nm). Emitted light passes through lens 18 and enters body fluid or tissue volume 60. It is recognized that one or more LEDs and/or other light emitting components may be included in light emitting portion 14. The number of LEDs or other opto-electronic light sources and corresponding light emission wavelengths will be selected according to the requirements of a particular application and will depend on the physiological condition being monitored.

The detecting portion 16 is formed from a modular sensor assembly 72 coupled to ferrule 40. Modular sensor assembly 72 includes two light detecting, opto-electronic components 46 and 48, circuit board 53, a wall 44 surrounding opto-electronic components 46 and 48, and a coating 64 for retaining wall 44 against circuit board 53. Opto-electronic components 46 and 48 are embodied as LEDs in one embodiment of the invention. LEDs 46 and 48 are mounted on printed circuit board 53 to enable appropriate electrical connections to LEDs 46 and 48. LEDs are formed from a direct band-gap semiconductor that emit narrow spectrum light when electrically biased in the forward direction of the p-n junction. Instead of biasing LEDs 46 and 48 to emit light, LEDs 46 and 48 are biased to generate current upon exposure to light, allowing LEDs 46 and 48 to function as light detectors, as generally disclosed in co-pending U.S. patent application Ser. No. 11/995,025. Wall 44 surrounds the LEDs 46 and 48 to promote light traveling through lens 38 to fall on LEDs 46 and 48. Wall 44 may share a common side with wall 24 in some embodiments, and may be formed from rigid, opaque or light-insulating material, such as a liquid crystal polymer. Alternatively, wall 44 can be formed from other, light insulating materials, for example any polymer material formed as a molded component, and may be non-rigid in some applications. Wall 44 may be attached to printed circuit board 53 using a coating 64 applied as a hard, die coat dam holding wall 44 to the board 53.

LEDs 46 and 48 are selected to match light emitting LEDs 26 and 28 such that one light-detecting LED 46 is sensitive to the same color of light emitted by LED 26 and the other light-detecting LED 48 is sensitive to the same color wavelength emitted by LED 28. In one embodiment, in which sensor assembly 10 is used for sensing blood oxygen saturation as described above, one of LEDs 26 and 28 is sensitive to red light (660 nm) and the other of LEDs 26 and 28 is sensitive to infrared light (890 nm). In another embodiment, in which sensor assembly 10 is used for sensing tissue perfusion, a third LED may be included for emitting near-infrared light (800 nm).

Circuit boards 52 and 53 are cut from a single circuit board on which both modular sensor assemblies 70 and 72 are formed. By implementing the light sources as LEDs 26 and 28 and light detectors as LEDs 46 and 48 that match LEDs 26 and 28, modular sensor assemblies 70 and 72 can be manufactured to be identical to each other. The functionality of modular sensor assembly 70 as a light emitting portion and modular sensor assembly 72 as a light detecting portion will be determined upon implementation of assemblies 70 and 72 within an IMD. As such, manufacturing processes for producing implantable optical sensor 10 are simplified by mass producing modular sensor assemblies which can be implemented as either light emitting portions or light detecting portions in a final optical sensor.

Although not shown in FIG. 1, it will be understood by one having skill in the art that the circuit board 52 includes integrated circuitry electrically coupled to LEDs 26 and 28 to deliver driver signals applied to LEDs 26 and 28 to activate LEDs 26 and 28. Likewise, integrated circuitry included on circuit board 53 is coupled to light detecting LEDs 46 and 48 to receive the current emitted by LEDs 46 and 48 in response to scattered light incident on LEDs 46 and 48 and providing the signal to processing circuitry configured to perform an algorithm for detecting a change in a physiological condition using the signal. Integrated circuitry may include an analog-to-digital converter and flash memory for digitizing the analog signal and providing the digitized signal to processing circuitry.

While opto-electronic components 26, 28, 46 and 48 are described as being LEDs in the illustrative embodiment shown in FIG. 1, modular assemblies may be built including any combination of opto-electronic components, including dedicated light emitting devices and/or dedicated light detecting devices. The modular assemblies are manufactured to include identical components, some of which may not be used upon implementation in an IMD. The components used and the functionality of the module will be determined upon implementation in the IMD.

Figure 2:
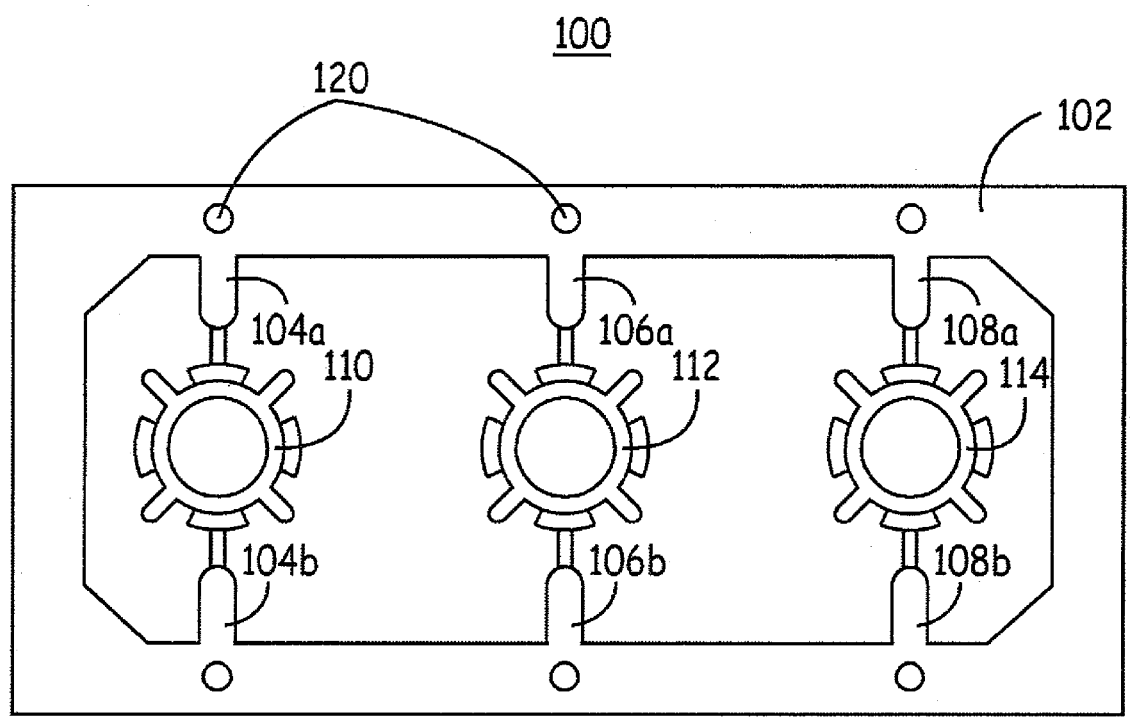
FIG. 2 is a top plan view of a molded framework including multiple walls for use in assembling modular optical sensor assemblies.

FIG. 2 is a top plan view of one embodiment of a molded framework including multiple walls for use in assembling modular optical sensor assemblies. Framework 100 is a plastic molded component including a frame 102 supporting multiple sets of arms 104a and 104b referred to collectively as 104, 106a and 106b referred to collectively as 106, and 108a and 108b referred to collectively as 108. Each set of arms 104, 106 and 108 extending from frame 102 supports a wall 110, 112, and 114, respectively. Each set of arms 104, 106, and 108 are shown to include two opposing arms in FIG. 2, however multiple walls 110, 112, and 114 held by framework 100 may each be supported by one or more arms in any desired physical arrangement. Framework 100 includes three walls 110, 112, and 114, however in other embodiments one or more walls may be supported by frame 102. Frame 102 includes multiple alignment pegs 120 for use in mounting and aligning framework 100 on a circuit board. In one embodiment, framework 100 is molded from a light-insulating material such as liquid crystal polymer.

Figure 3A:
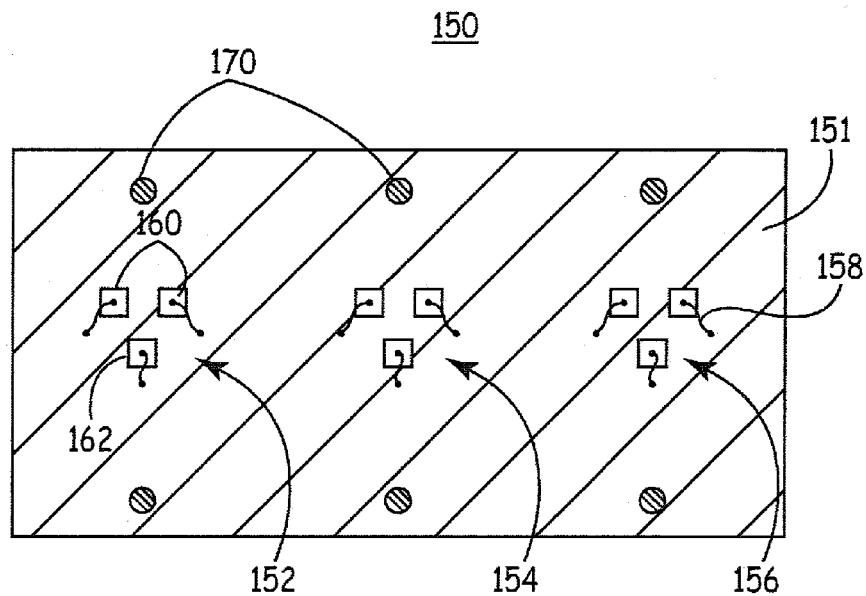
FIG. 3A is a top plan view of a printed circuit board for use in assembling modular optical sensor assemblies.

FIG. 3A is a top plan view of a printed circuit board 150 for use in assembling modular optical sensor assemblies. Multiple sets 152, 154, and 156 of opto-electronic components are mounted on a top surface 151 of circuit board 150. Each opto-electronic component is electrically coupled by a conductive element 158 to circuitry (not shown) implemented on the opposite side of the circuit board 150. Each set of opto-electronic components 152, 154 and 156 may include light emitting, light detecting, or a combination of both light emitting and light detecting components. In one embodiment, each set 152, 154 and 156 includes at least one light emitting component 160 and at least one light detecting component 162. For example, the opto-electronic component sets 152, 154 and 156 may include LEDs which can be configured as light emitting devices or light detecting devices as described above. In an alternative embodiment, components 160 are provided as LEDs for emitting light and component 162 is provided as a photodetector. Each component set 152, 154, and 156 is provided with identical components 160 and 162 such that multiple identical modular sensor assemblies can be produced from circuit board 150. The functionality of the modular assemblies, i.e. as light emitting or light detecting assemblies, is determined upon implementation of the assemblies in an IMD. Circuit board 150 further includes holes 170 for receiving alignment pegs 120 of framework 100 (FIG. 2).

Figure 3B:
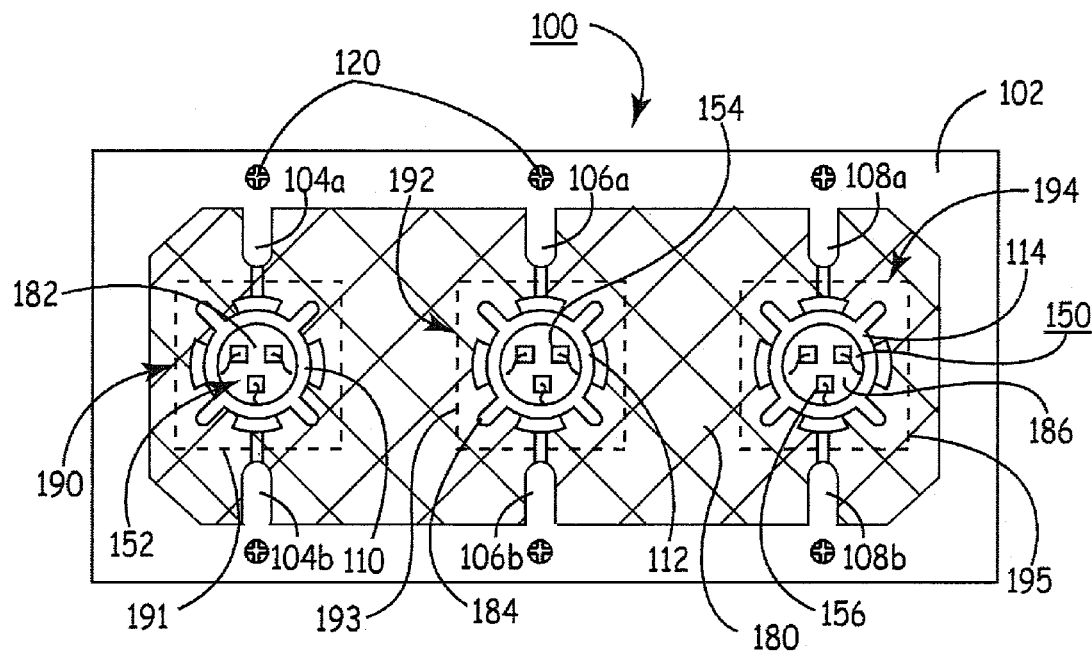
FIG. 3B is a top plan view of a circuit board with the framework shown in FIG. 2 mounted thereon.

FIG. 3B is a top plan view of circuit board 150 with framework 100 mounted thereon. Alignment pegs 120 are aligned and inserted in circuit board holes 170 (not visible in FIG. 3B) to promote proper alignment of walls 110, 112, and 114 around opto-electronic component sets 152, 154 and 156. Walls 110, 112, and 114 each completely surround the opto-electronic component sets 152, 154 and 156, respectively, and provide optical insulation to the enclosed components. With framework 100 securely aligned on circuit board 150, a coating 180 is applied to circuit board 150 by partially filling framework 100. Coating 180 is not applied in the areas 182, 184 and 186 that are enclosed by walls 110, 112, and 114. Circuit board 150 remains exposed in those areas.

In some embodiments, an optical coupling member may be formed by applying a coating of an optical material within walls 110, 112, and 114 for improving optical coupling between the opto-electronic components 152, 154, and 156 and a lens used in forming an optical sensor as generally disclosed in co-pending U.S. patent application Ser. No. 11/955,056, hereby incorporated herein by reference in it's entirety. Coating 180 and a coating applied within walls 110, 112, and 114 may or may not be formed using the same material. As such, depending on the optical properties of coating 180, coating 180 may also be applied within walls 110, 112, and 114, in areas 182, 184, and 186.

In one embodiment, coating 180 is formed of an epoxy material. After curing, each of the opto-electronic component sets 152, 154 and 156 may undergo electrical testing. Each wall 110, 112, and 114 and enclosed set of opto-electronic components 152, 154 and 156, along with corresponding electrical circuitry implemented on the bottom side form a modular optical sensor assembly 190, 192, and 194, respectively. After coating 180 cures and after any desired electrical testing, circuit board 150, coating 180, and framework 100 are cut, for example, along the dashed lines 191, 193, and 195 to form individual modular optical sensor assemblies 190, 192, and 194. Frame 102, arm sets 104, 106 and 108 and outer areas of circuit board 150 are cut away and discarded. The remaining modular sensor assemblies 190, 192, and 194 can then be used in assembling an implantable optical sensor in an IMD.

Figure 4A:
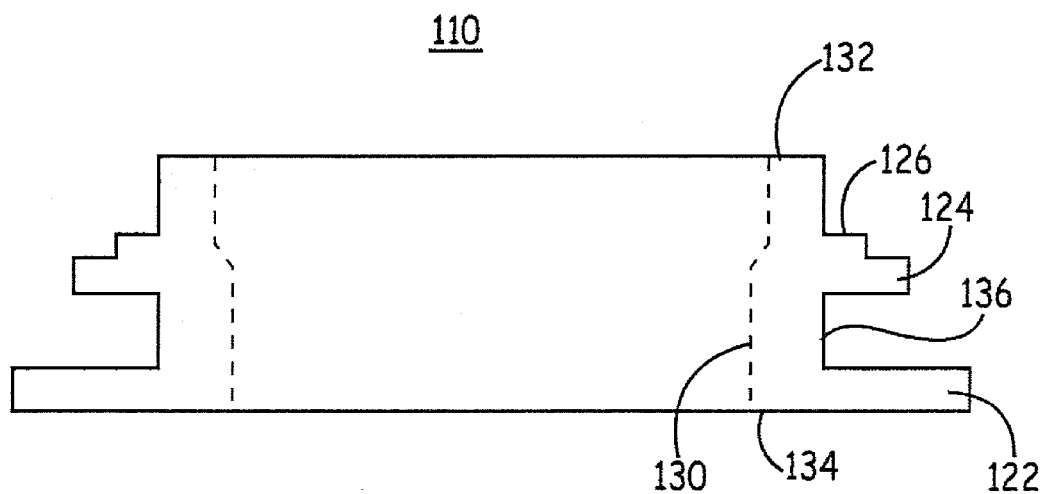
FIG. 4A is a side plan view and FIG. 4B is a top plan view of a wall used in manufacturing a modular optical sensor assembly according to one embodiment of the invention.
Figure 4B:
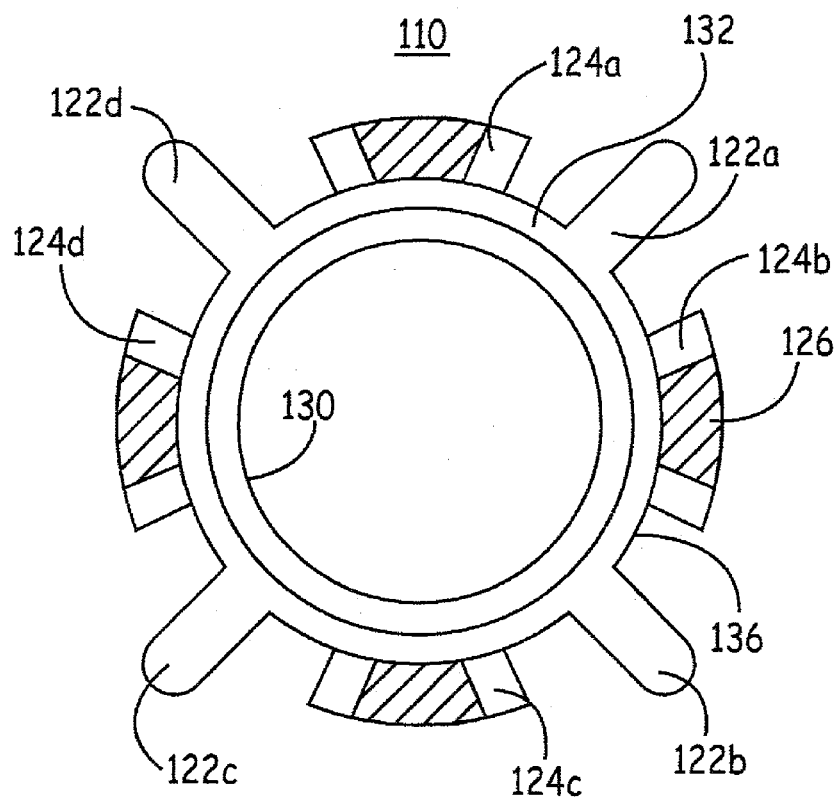

FIG. 4A is a side plan view and FIG. 4B is a top plan view of a wall 110 used in manufacturing a modular optical sensor assembly according to one embodiment of the invention. Wall 110 is formed having an inner surface 130 and an outer surface 136 separated by top edge 132 and bottom edge 134. Top and bottom edges 132 and 134 are parallel to each other, and bottom edge 134 is formed substantially flat to interface with the top surface 151 of printed circuit board 150 (shown in FIG. 3A). Inner and outer surfaces 130 and 136 may be substantially parallel, extending generally perpendicular to top and bottom edges 132 and 134. In some embodiments, inner wall surface 130 may be provided with a reflective coating.

Wall 110 includes a first flange 122 extending radially outward from outer surface 136. First flange 122 may be continuous around the entire outer surface 136 or discontinuous, including multiple sections 122a, 122b, 122c and 122d as shown in FIG. 4B. First flange 122 is located immediately adjacent or proximate to bottom edge 134 such that first flange 122 becomes embedded within coating 180 shown in FIG. 3B. First flange 122, embedded in coating 180, acts as a mechanical interlock with coating 180 to retain wall 110 against circuit board 150, and thereby maintain proper alignment of wall 110 relative to enclosed opto-electronic components.

Wall 110 further includes a second flange 124 located above first flange 122, i.e. closer to top edge 132. Second flange 124 may be continuous around outer surface 136 or discontinuous, including multiple sections 124a, 124b, 124c and 124d, as seen in the top view of FIG. 4b. Second flange 124 includes a stop surface 126 for interfacing with a ferrule to which wall 110 becomes coupled for assembly of a hermetically-sealed optical sensor in an IMD.

While flanges 122 and 124 are shown extending outward from outer wall surface 136, it is recognized that wall 110 could be configured to provide a stop surface 126 extending from an inner surface of wall 110. Furthermore, in embodiments including a coating applied to the interior of wall 110, i.e. the area encircled by wall 110, flange 122 could additionally or alternatively extend inward from inner surface 130.

Figure 5:
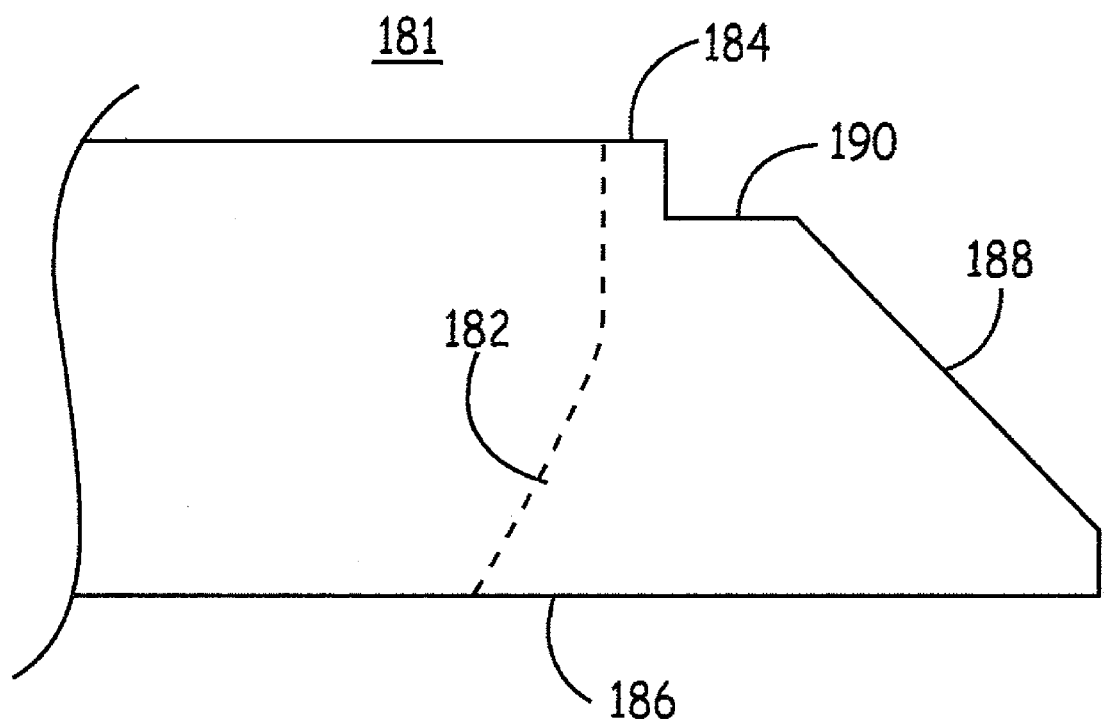
FIG. 5 is a partial side plan view of a wall for use in a modular optical sensor assembly according to an alternative embodiment of the invention.

In alternative embodiments, one or both of inner surface 130 and outer surface 136 may be angled or sloped relative to the parallel top and bottom edges 132 and 134. For example, as shown in the partial side plan view of FIG. 5, a wall 181 is formed having an outer surface 188 sloping outward beginning from top edge 184 to bottom edge 186 to provide a large surface area for interfacing with coating 180 (shown in FIG. 3B). Outward sloping outer surface 188 will become embedded within coating 180 such that wall 181 is mechanically retained by hardened coating 180.

Inner wall 182 is shown sloping inward from top edge 184 to bottom edge 186. Inner wall 182 may be formed to promote the direction of light toward opto-electronic components or toward a lens. Inner wall 182 may be formed to interface with a coating applied to the circuit board within the interior of wall 181 for use as a optical coupling member as well as for retaining wall 181 against a circuit board.

In the embodiments illustrated herein, wall 110 is shown having a generally circular shape as shown in the top view of FIG. 4B. Embodiments of the invention, however, are not limited to a circular-shaped wall. In other embodiments, walls for surrounding opto-electronic components may be formed having generally oval, triangular, square, rectangular, or other shapes for surrounding or encircling opto-electronic components. As used herein, "wall" refers to any structure, which may be formed in one or more sections assembled to completely encircle electronic components mounted on a circuit board. In the illustrative embodiments presented herein, the electronic components are opto-electronic components and configured to emit or receive light through a lens mounted over the opto-electronic components. The wall provides a light-insulating barrier surrounding the components.

Embodiments of the invention are not limited to modular assemblies having light-insulating walls encircling opto-electronic components, however. Modular assemblies for use in manufacturing implantable medical devices may include walls coupled to a circuit board and encircling electronic components to protect the encircled components from light, heat, fluids or any other environmental factor that may compromise the optimal functioning of the electronic components. Alternatively, the wall may protect IMD components exterior to the wall from light or heat generated by the components encircled by the wall.

Figure 6:
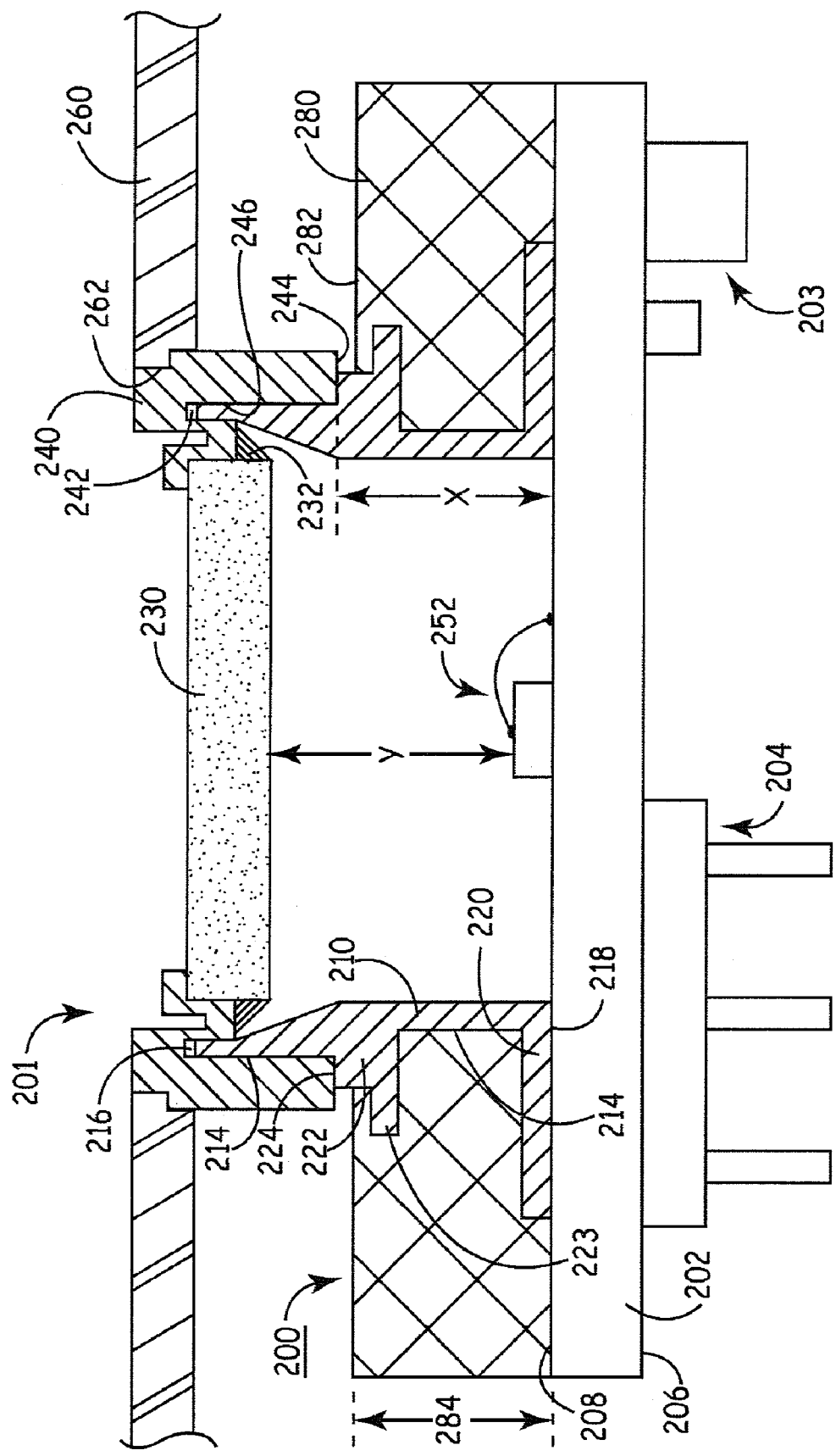
FIG. 6 is a side sectional view of a single modular sensor assembly assembled within an IMD housing.

FIG. 6 is a side sectional view of a single modular sensor assembly 200 assembled within an IMD housing 260 and coupled to a ferrule 240. Modular sensor assembly 200 includes a printed circuit board 202 having a top surface 208 on which a set of opto-electronic components 252 has been mounted. The opto-electronic components 252 are electrically coupled to electronic circuitry 203 and an electrical connector 204 provided on the bottom side 206 of circuit board 202. Modular sensor assembly 200 further includes wall 210 positioned on circuit board 202 encircling opto-electronic component set 252. Wall bottom edge 218 is retained against circuit board top surface 208 by coating 280. Coating 280 is applied to top surface 208 with a height or thickness 284 such that coating 280 interfaces with wall outer surface 214. Depending on the materials used to form coating 280 and wall 210, coating 280 may or may not form a chemical or adhesive bond with wall 210. As such, wall 210 may be formed with a first flange 220 that becomes embedded in coating 280 to form a mechanical interlock between coating 280 and wall 210 and thereby entrap wall 210 against circuit board 202.

In alternative embodiments, wall 210 may be secured to circuit board 202 using localized "tack bonds" or a bead of adhesive dispensed continuously or in segments along the meeting point between wall outer surface 214 and circuit board top surface 208. An adhesive could alternatively be applied between wall bottom edge 218 and circuit board top surface 208. It is expected that coating 280 will provide the greatest light insulation to opto-electronic components 252 as well as provide protection to wire bonds formed on circuit board top surface 208.

Wall 210 includes a stop surface 224 for interfacing with ferrule 240. A top surface 282 of coating 280 is formed below stop surface 224 such that stop surface 224 remains exposed to interface with ferrule bottom edge 244. Top edge 216 of wall 210 can be inserted into groove 242 of ferrule 240 until stop surface 224 and ferrule bottom edge 244 meet. A lens 230 is coupled to ferrule 240 at gold braze joint 232. Wall 210 is formed such that stop surface 244 is a distance X from circuit board top surface 208. As such, a distance Y between lens 230 mounted in ferrule 240 and an opto-electronic device 252 is controlled by the dimension X of wall 210 to be a desired distance when ferrule bottom edge 244 meets stop surface 224. In other words, stop surface 224 is positioned such that a controlled press fit attachment between ferrule 240 and wall 210 promotes proper spatial positioning of opto-electronic device(s) 252 relative to lens 230. In other embodiments, the top surface 282 of coating 280 may be used as a stop surface for meeting ferrule bottom edge 244, however, less control over the exact thickness 284 of coating 280 may result in inconsistent distance Y between lens 230 and component set 252.

A gap between top surface 216 of wall 210 and the ferrule 240 remains after interfacing ferrule bottom edge 244 against stop surface 224. As such, ferrule 240 and wall 210 interface at a stop surface 224 formed in a single plane. Forming a stop surface 224 in a single plane promotes a consistent fit between ferrule 240 and wall 210 and thus a consistent stand-off distance between lens 230 and opto-electronic component(s) 252. Stop surface 224 may be continuous around the outer surface 214 of wall 210 or formed in multiple sections as generally shown in FIG. 4B wherein stop surface 126 is formed on flange sections 124a through 124d. In one embodiment, stop surface 224 may include three, co-planar sections spaced apart around wall outer surface 214 to minimize rocking of ferrule 240 on wall 210.

Stop surface 224 is shown formed as part of a second flange 222, extending outward from wall outer surface 214, above first flange 220, i.e., closer to wall top edge 216. A portion 223 of second flange 222 may optionally be embedded in coating 280 to aid in retaining wall 210 against circuit board 202.

Wall 210 is sized to form a press fit within ferrule groove 242. Interference between wall outer surface 214 and ferrule inner surface 246 forming ferrule groove 242 acts to retain wall 210 within ferrule 240. It is recognized that ferrule 240 and wall 210 may be formed with other interlocking features to form a press fit that securely couples wall 210 with ferrule 240. For example, rather than ferrule 240 sliding down along a wall outer surface 214 as shown in FIG. 6, ferrule 240 may slide into a groove formed in wall 210 or in a groove formed between redundant walls attached to circuit board 202. In various embodiments, an adhesive could additionally or alternatively be used between wall 210 and ferrule 240 to fixedly attach wall 210 to ferrule 240.

Prior to assembling modular sensor assembly 200 with ferrule 240, lens 230 is coupled to ferrule 240, and ferrule 240 is coupled to IMD housing 260. Ferrule 240 is typically welded into an opening 262 formed in housing 260. Opening 262 in housing 260, ferrule 240 and lens 230 form a window assembly 201, which when assembled with modular sensor assembly 200 forms an implantable optical sensor.

In one assembly method, window 201 is fully assembled first and then modular sensor assembly 200 is assembled with window 201 by joining ferrule 240 and wall 210. In an alternative assembly method, modular sensor assembly 200 is assembled with ferrule 240 and lens 230 and then the entire assembly is then coupled to housing 260. An adhesive bond may also be applied between coating top surface 282 and housing 260 or between the bottom surface 206 of circuit board 202 and an opposite housing shield half (not shown in FIG. 6) to secure modular sensor assembly within housing 260.

Figure 7:
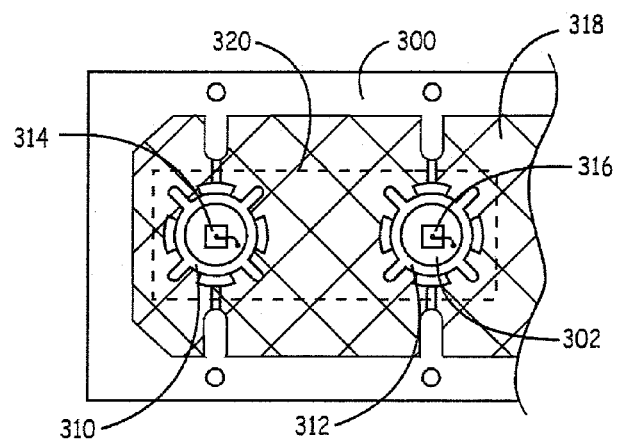
FIG. 7 is a partial top plan view of a framework positioned on a circuit board according to an alternative embodiment of the invention.

FIG. 7 is a partial top plan view of a framework 300 positioned on a circuit board 302. It is recognized that in alternative embodiments, a single modular sensor assembly may include two or more walls each encircling a respective opto-electronic component(s). Framework 300 supports walls 310 and 312. Wall 310 encloses a light emitting component(s) 314, and wall 312 encloses a light detecting component(s) 316, both mounted on circuit board 302. A coating 318 applied to circuit board 302 fills framework 300, along the outer surfaces of walls 310 and 312 to thereby retain walls 310 and 312 against circuit board 302. After coating 318 has cured, a single modular sensor assembly 320 is cut from circuit board 302, as indicated by dashed line. In this embodiment, the individual modular sensor assembly includes two walls 310 and 312 enclosing two different sets of opto-electronic components 314 and 316. It is recognized that a circuit board and corresponding framework may be built to include any number of opto-electronic component sets and any corresponding number of walls to enclose the opto-electronic components. Likewise, a single modular assembly may include one or more of the opto-electronic component sets, each set being encircled by a wall fixed to the circuit board.

Figure 8A:
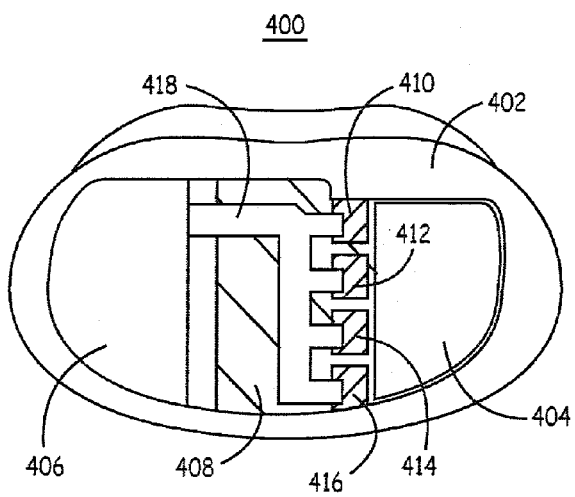
FIG. 8A is plan view of an IMD housing shield half in which multiple modular optical sensor assemblies have been assembled.

FIG. 8A is plan view of an IMD housing shield half in which multiple modular sensor assemblies have been assembled. IMD 400 includes IMD circuitry 406 coupled to a battery 404 and capacitors 408 assembled in shield half 402. Shield half 402 will be assembled with a second shield half (not shown) to form a hermetically sealed IMD housing. Multiple modular optical sensor assemblies 410, 412, 414 and 416 have been assembled in shield half 402. Each modular optical sensor assembly is coupled to a flex circuit 418 to allow connection of modular sensor assemblies 410 through 416 to IMD circuitry 406.

Figure 8B:
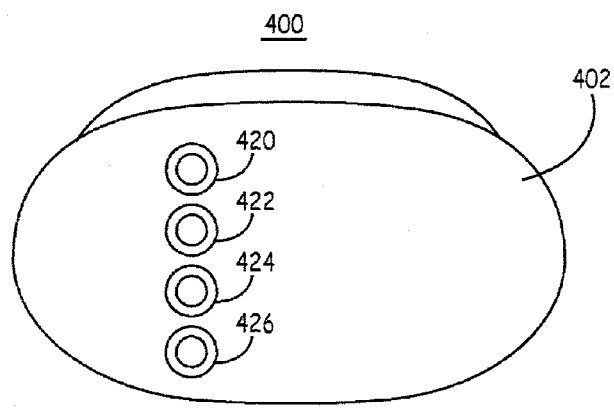
FIG. 8B is a plan view of the outer surface of the shield half shown in FIG. 8A.

FIG. 8B is a plan view of the outer surface of the shield half 402 shown in FIG. 8A. Optical sensor windows 420, 422, 424, and 426 are formed in shield half 402 in a manner that maintains hermeticity of the IMD housing. As described previously, each sensor window 420 through 426 includes a ferrule 430 welded within an opening 436 in shield half 402. A lens 432 is mounted and hermetically coupled to ferrule 430. A modular sensor assembly 410 through 416 (FIG. 8A) is aligned with and coupled to a respective sensor window 420 through 426. It is recognized that one or more modular assemblies including one or more walls encircling electronic components may be assembled within an IMD and with other IMD components in any suitable arrangement.

Figure 9:
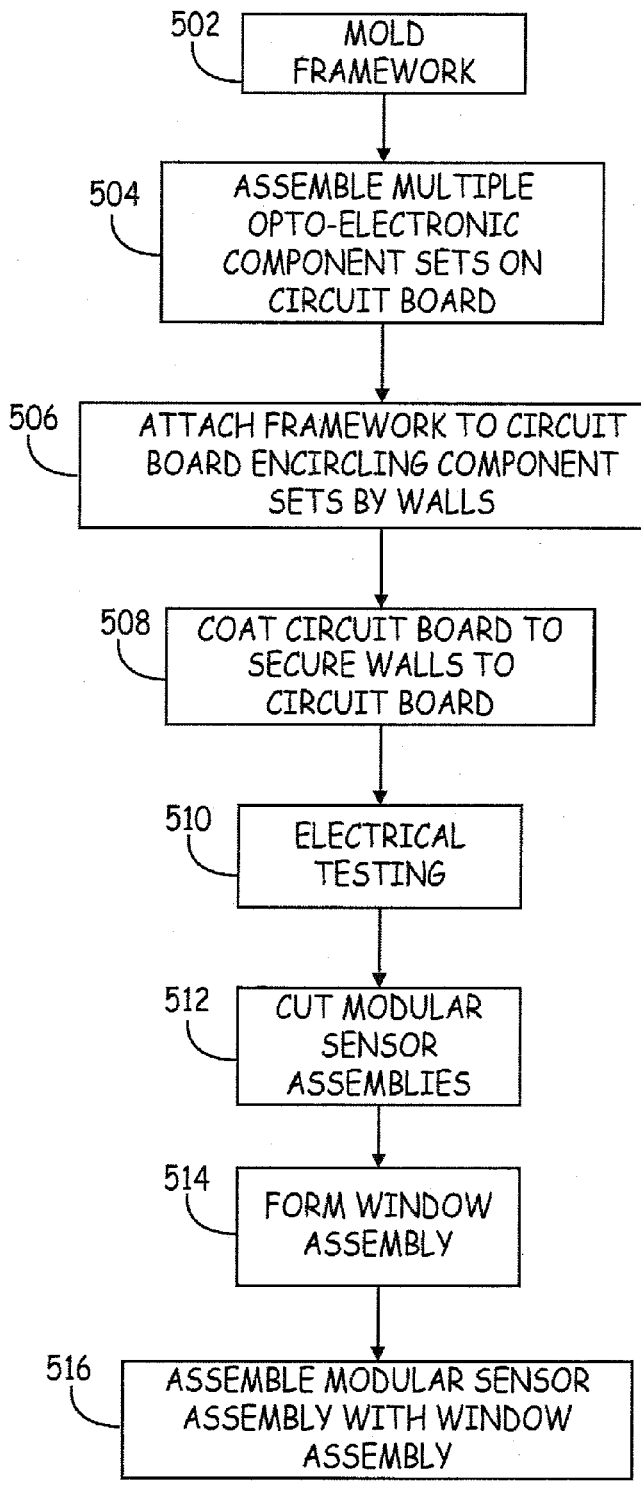
FIG. 9 is a flow chart of a method for manufacturing an implantable optical sensor according to one embodiment of the invention.

FIG. 9 is a flow chart of a method for manufacturing an implantable optical sensor according to one embodiment of the invention. At block 502, a framework is molded to include one or more walls supported by arms extending from an outer frame. The framework is molded from a light-insulating material.

At block 504, one or more opto-electronic component sets, each set including one or more light-emitting and/or light detecting component, are assembled on a circuit board. The framework is attached to the circuit board at block 506, for example using a peg-in-hole attachment mechanism as described previously. The framework is aligned and attached to the circuit board such that each wall supported by the framework encircles a respective opto-electronic component set.

At block 508, the circuit board is coated by filling the framework with a coating material to form a desired coating thickness. The coating secures the walls to the circuit board as described previously. After the coating cures, electrical testing of the opto-electronic components may be performed at block 510 to ensure proper functioning of the components.

At block 512, modular sensor assemblies are cut from the circuit board. Cutting is performed using, for example but not limited to, a saw, water jet, rotating bit, or laser cutting method. A window assembly is formed in an opening in the housing of an IMD at block 514 by hermetically sealing a ferrule in the IMD opening and hermetically coupling a lens within the ferrule. A modular sensor assembly is then assembled with the window assembly at block 516 by joining the wall with the ferrule, thereby forming a hermetically-sealed optical sensor within an IMD. The final assembly may further include applying a coating, such as a silicon coating, over the lens and ferrule outer surface to protect the gold braze joint as described in conjunction with and shown in FIG. 1.

Thus, a modular assembly for use with an IMD and associated method of manufacture have been presented in the foregoing description with reference to specific embodiments. It is appreciated that various modifications to the referenced embodiments may be made without departing from the scope of the invention as set forth in the following claims.

The invention claimed is:

1. An manufacturing assembly, comprising:
   a plurality of modular sensor assemblies, each of the plurality of modular sensor assemblies comprising:
      a circuit board; and
      a plurality of electronic components mounted on a top surface of the circuit board, multiple ones of the plurality of electronic components being mounted in a location on the circuit board corresponding to a location for each of the plurality of modular sensor assemblies;
   a framework, comprising:
      a supporting structure; and
      a wall for each of the modular sensor assemblies, the walls being supported by the supporting structure and having an outer surface and an inner surface separated by a top edge and a bottom edge, the bottom edge configured to be positioned against the circuit board;
      wherein the wall comprises a first flange extending from the wall proximate the bottom edge; and
   a coating applied to the circuit board top surface along the wall for coupling the wall to the circuit board and providing additional isolation against light for the electronic component, the first flange embedded in the coating for retaining the wall bottom edge against the circuit board;
   wherein each of the plurality of modular sensor assemblies is isolated from an emission of an electronic component of another one of the plurality of modular sensor assemblies.

2. The manufacturing assembly of claim 1 further comprising:
   a window formed in a housing; and
   a ferrule mounted in the window, said ferrule comprising a groove for receiving the top wall edge and providing additional isolation against light for the electronic component.

3. The manufacturing assembly of claim 2 wherein the ferrule groove and wall outer surface form an interference fit for retaining the top wall edge within the groove.

4. The manufacturing assembly of claim 2 wherein the modular sensor assembly further comprises a stop surface for interfacing with the ferrule.

5. The manufacturing assembly of claim 4 wherein the wall further comprises a second flange, the stop surface formed on the second flange and not embedded in the coating.

6. The manufacturing assembly of claim 4 wherein the stop surface is formed at a height from the wall bottom edge for controlling a distance between the window and the electronic component.

7. The manufacturing assembly of claim 5 wherein one of the first flange and the second flange extends from the wall outer surface.

8. The manufacturing assembly of claim 2 wherein the electronic component is an opto-electronic component and the wall is formed from a light-insulating material.

9. The manufacturing assembly of claim 8 further comprising a lens mounted in the ferrule over the opto-electronic device.

10. The manufacturing assembly of claim 9 further comprising an optical coating applied along the lens and ferrule.

11. A method for manufacturing a plurality of modular sensor assemblies, comprising the steps of:
    molding a framework comprising a wall for each of the modular sensor assemblies, the walls supported by a supporting structure and having an outer surface and an inner surface separated by a top edge and a bottom edge;
    mounting a plurality of electronic components on a top surface of a circuit board, multiple ones of the plurality of electronic components being mounted in a location on the circuit board corresponding to a location for each of the plurality of modular sensor assemblies; then
    coupling the framework to the top surface of the circuit board, the bottom edge of the wall being positioned against the circuit board, wherein each wall of each one of the plurality of modular sensor assemblies encircles corresponding multiple ones of the plurality of electronic components of each corresponding one of the plurality of modular sensor assemblies to provide isolation against at least one of light, heat and fluid for electronic components of each modular sensor assembly; and then
    applying a coating to the circuit board top surface along the wall for coupling the wall to the circuit board and providing additional isolation against light for the electronic component, wherein the wall comprises a first flange extending from the wall proximate the bottom edge, the first flange being embedded in the coating for retaining the wall bottom edge against the circuit board; and then
    cutting the plurality of modular sensor assemblies out of the circuit board.

12. The method of claim 11 further comprising
    forming a window in the housing;
    mounting a ferrule in the window, the ferrule comprising a groove for receiving the top wall edge and providing additional isolation against light for the electronic component; and
    coupling the modular sensor assembly to the hermetically sealed housing by inserting the top wall edge into the ferrule groove.

13. The method of claim 12 wherein the ferrule groove and wall outer surface form an interference fit for retaining the top wall edge within the groove.

14. The method of claim 12 wherein molding the framework further comprises forming a stop surface for interfacing with the ferrule.

15. The method of claim 14 wherein the wall further comprises a second flange, the stop surface formed on the second flange and not embedded in the coating.

16. The method of claim 14 wherein the stop surface is formed at a height from the wall bottom edge for controlling a distance between the window and the electronic component.

17. The method of claim 15 wherein one of the first flange and the second flange extends from the wall outer surface.

18. The method of claim 12 wherein the electronic component is an opto-electronic component and the wall is formed from a light-insulating material.

19. The method of claim 18 further comprising mounting a lens in the ferrule.

20. The method of claim 18 further comprising applying an optical coating along the lens and ferrule.

21. The method of claim 11 wherein molding the framework comprises forming the supporting structure by mounting pegs along a frame and wherein coupling the framework on the circuit board top surface comprises aligning the mounting pegs with holes formed in the circuit board top surface.

22. The method of claim 21 wherein applying the coating comprises filling a portion of the framework with a coating material.

23. The manufacturing assembly of claim 1 wherein the coating has a thickness such that the coating interfaces with the outer surface of the wall.

24. The manufacturing assembly of claim 23 wherein the flange has a height relative to said bottom edge and wherein the thickness of the coating is at least as great as the height of the flange.

25. The method of claim 11 wherein the applying the coating step applies the coating to a thickness such that the coating interfaces with the outer surface of the wall.

26. The method of claim 25 wherein the flange has a height relative to said bottom edge and wherein the applying the coating step applies the coating with the thickness of the coating being at least as great as the height of the flange.

* * * * *